United States Patent
Kaminski (10) Patent No.: US 11,583,218 B2
(45) Date of Patent: Feb. 21, 2023

(54) EMG DEVICE

(71) Applicant: Advancer Technologies, LLC, Raleigh, NC (US)

(72) Inventor: Brian Eugene Kaminski, Raleigh, NC (US)

(73) Assignee: Advancer Technologies, LLC, Raleigh, NC (US)

( * ) Notice: Subject to any disclaimer, the term of this patent is extended or adjusted under 35 U.S.C. 154(b) by 408 days.

(21) Appl. No.: 16/689,650

(22) Filed: Nov. 20, 2019

(65) Prior Publication Data

US 2021/0145302 A1 May 20, 2021

(51) Int. Cl.
*A61B 5/00* (2006.01)
*A61B 5/389* (2021.01)
*H03F 3/45* (2006.01)

(52) U.S. Cl.
CPC ............ *A61B 5/389* (2021.01); *A61B 5/7225* (2013.01); *H03F 3/45* (2013.01); *A61B 2562/04* (2013.01); *A61B 2562/225* (2013.01); *H03F 2200/102* (2013.01); *H03F 2200/168* (2013.01)

(58) Field of Classification Search
CPC ......... H03F 2200/168; H03F 2200/105; H03F 2200/102; H03F 3/45; H03F 3/45475; H03F 2203/45138; A61B 2562/22; A61B 2562/227; A61B 2562/225; A61B 2562/166; A61B 2562/164; A61B 2562/16; A61B 2562/06; A61B 5/7228; A61B 5/7221; A61B 5/7225; A61B 5/4005; A61B 5/389; A61B 5/725; A61B 2562/04
See application file for complete search history.

(56) References Cited

U.S. PATENT DOCUMENTS

| | | | |
|---|---|---|---|
| 4,170,225 A | 10/1979 | Criglar et al. |
| 4,467,813 A | 8/1984 | Schomburg |
| 4,540,000 A | 9/1985 | Doherty et al. |
| 4,807,642 A | 2/1989 | Brown |
| 4,811,742 A | 3/1989 | Hassel et al. |
| 6,289,245 B1 | 9/2001 | Mo et al. |
| 6,411,843 B1 | 6/2002 | Zarychta |

(Continued)

OTHER PUBLICATIONS

AB Electronics UK. "Raspberry Pi Expansion Boards and Accessories." 2014, pp. 1-2. [Retrieved on Jul. 17, 2015], Retrieved from Internet: https://www.abelectronics.co.uk/.

(Continued)

*Primary Examiner* — May A Abouelela
(74) *Attorney, Agent, or Firm* — Carlson, Gaskey & Olds, P.C.

(57) ABSTRACT

An electromyography (EMG) device according to an aspect of the present disclosure includes a main circuit board having opposing first and second faces. A plurality of first connectors of a first type are provided on the first face, and a plurality of input contacts are provided on the second face. An EMG circuit is provided on the main circuit board. The EMG circuit is configured to utilize the input contacts as inputs to obtain an EMG input signal, and process the EMG input signal to provide an EMG output signal that is based on, but different from, the EMG input signal. For each of the input contacts, there is no conductive path directly between the input contact and any of the first connectors.

23 Claims, 6 Drawing Sheets

(56) References Cited

U.S. PATENT DOCUMENTS

| | | | |
|---|---|---|---|
| 6,532,383 B2 | 3/2003 | Maloney et al. | |
| 7,286,871 B2 | 10/2007 | Cohen | |
| 7,809,435 B1 | 10/2010 | Ettare et al. | |
| 7,896,807 B2 | 3/2011 | Clancy et al. | |
| 8,170,656 B2 | 5/2012 | Tan et al. | |
| 8,386,026 B2 | 2/2013 | Fink et al. | |
| 8,386,244 B2 | 2/2013 | Ricci et al. | |
| 10,814,166 B1* | 10/2020 | Uehara | A61B 5/4519 |
| 11,484,242 B2* | 11/2022 | Ang | A61B 5/389 |
| 2008/0200827 A1 | 8/2008 | Cyphery et al. | |
| 2008/0312520 A1* | 12/2008 | Rowlandson | A61N 1/048 600/372 |
| 2009/0099473 A1* | 4/2009 | Dunseath | A61B 5/6814 600/383 |
| 2009/0292194 A1 | 11/2009 | Libbus et al. | |
| 2011/0251512 A1 | 10/2011 | Fink et al. | |
| 2011/0279963 A1* | 11/2011 | Kumar | A61B 5/291 156/60 |
| 2012/0022347 A1* | 1/2012 | Liu | A61B 5/14532 600/587 |
| 2012/0029322 A1* | 2/2012 | Wartena | A61B 5/4812 600/301 |
| 2012/0188158 A1* | 7/2012 | Tan | G06N 20/00 345/156 |
| 2012/0209134 A1* | 8/2012 | Morita | G06N 20/00 600/546 |
| 2012/0330126 A1* | 12/2012 | Hoppe | A61B 5/14552 600/300 |
| 2014/0206976 A1* | 7/2014 | Thompson | G16Z 99/00 600/391 |
| 2014/0275748 A1 | 9/2014 | Dunki-Jacobs et al. | |
| 2014/0309547 A1 | 10/2014 | Linderman | |
| 2014/0371568 A1* | 12/2014 | Selby | H01R 12/79 29/882 |
| 2015/0045689 A1 | 2/2015 | Barone | |
| 2015/0057770 A1* | 2/2015 | Bailey | G06F 3/015 700/83 |
| 2015/0072326 A1* | 3/2015 | Mauri | A63B 24/0006 434/247 |
| 2015/0080675 A1* | 3/2015 | Shin | A61B 5/721 600/301 |
| 2015/0155912 A1 | 6/2015 | Winward et al. | |
| 2015/0272457 A1* | 10/2015 | Etemad | A61B 5/316 600/509 |
| 2016/0051182 A1* | 2/2016 | Zabaleta Rekondo | A61B 5/389 600/388 |
| 2016/0128594 A1* | 5/2016 | Amir | A61B 5/746 600/382 |
| 2016/0157717 A1* | 6/2016 | Gaster | A61B 8/02 600/301 |
| 2016/0317058 A1* | 11/2016 | Kaminski | A61B 5/7225 |
| 2017/0119255 A1* | 5/2017 | Mahajan | A61B 7/003 |
| 2017/0135626 A1* | 5/2017 | Singer | A61B 5/369 |
| 2017/0196513 A1* | 7/2017 | Longinotti-Buitoni | A61B 5/7405 |
| 2017/0238812 A1* | 8/2017 | Atlas | A61B 5/1117 |
| 2017/0340855 A1* | 11/2017 | Soulet De Brugiere | A61B 5/6814 |
| 2018/0008196 A1* | 1/2018 | Connor | A61B 5/6828 |
| 2018/0153430 A1* | 6/2018 | Ang | A61B 5/4851 |
| 2018/0184939 A1* | 7/2018 | Christiansen | A61B 5/6833 |
| 2018/0199849 A1* | 7/2018 | Axelrod | A61B 5/08 |
| 2018/0229025 A1* | 8/2018 | Wheeler | A61N 1/3606 |
| 2018/0307314 A1* | 10/2018 | Connor | A61B 5/1123 |
| 2018/0317770 A1* | 11/2018 | Ortega | A61B 5/02055 |
| 2018/0345079 A1* | 12/2018 | Lindman | A61B 5/318 |
| 2018/0369568 A1* | 12/2018 | Ishibe | A61B 5/05 |
| 2019/0008450 A1* | 1/2019 | Gurievsky | A61B 5/4812 |
| 2019/0008453 A1* | 1/2019 | Spoof | A61B 5/4035 |
| 2019/0082987 A1* | 3/2019 | Varpula | A61B 5/6804 |
| 2019/0142339 A1* | 5/2019 | Thommandram | A61B 5/4884 600/388 |
| 2019/0159731 A1* | 5/2019 | Cavallari | A61B 5/747 |
| 2019/0175110 A1* | 6/2019 | Gregersen | A61B 1/00148 |
| 2019/0200891 A1* | 7/2019 | Jung | A61B 5/296 |
| 2019/0216354 A1* | 7/2019 | Sternberger | A61B 5/389 |
| 2019/0247650 A1* | 8/2019 | Tran | A61N 1/025 |
| 2019/0290137 A1* | 9/2019 | Zhang | A61B 5/14532 |
| 2019/0307399 A1* | 10/2019 | Gutierrez | G02C 7/083 |
| 2019/0320930 A1* | 10/2019 | Derkx | A61B 5/7203 |
| 2019/0336073 A1* | 11/2019 | Kirkup | A61B 5/389 |
| 2019/0343661 A1* | 11/2019 | Messner | A61B 5/296 |
| 2020/0054285 A1* | 2/2020 | Lemons | A61N 1/0492 |
| 2020/0069943 A1* | 3/2020 | Campean | A61B 5/7221 |
| 2020/0085365 A1* | 3/2020 | McDonald | A61B 8/0866 |
| 2020/0121210 A1* | 4/2020 | Herr | A61F 2/6607 |
| 2020/0187808 A1* | 6/2020 | Yang | A61B 5/291 |
| 2020/0367823 A1* | 11/2020 | Chahine | A41B 11/00 |
| 2021/0000351 A1* | 1/2021 | Murali | A61B 5/6833 |
| 2021/0015419 A1* | 1/2021 | Karjalainen | A61B 5/7235 |
| 2021/0052418 A1* | 2/2021 | Breiter | A61B 5/4561 |
| 2021/0059546 A1* | 3/2021 | Myllykangas | A61B 5/24 |
| 2021/0137400 A1* | 5/2021 | Mirov | A61B 5/319 |
| 2021/0137457 A1* | 5/2021 | Matsumoto | A61B 5/0008 |
| 2021/0162262 A1* | 6/2021 | Lee | A63B 23/0494 |
| 2021/0212621 A1* | 7/2021 | Niijima | A61B 5/389 |
| 2021/0290108 A1* | 9/2021 | Hirai | A61B 5/1126 |
| 2021/0315509 A1* | 10/2021 | Farina | A61B 5/395 |
| 2022/0019284 A1* | 1/2022 | Kaifosh | G06F 3/016 |
| 2022/0022801 A1* | 1/2022 | Wendelken | G06N 7/00 |

OTHER PUBLICATIONS

Freetronics Pty Ltd. "Stacking Arduino Shields." 2010-2015, pp. 1-3 (156). [Retrieved on Jul. 17, 2015], Retrieved from Internet: http://www.freetronics.com.au/pages/stacking-arduino-shields#.ValYRfm6daR.

Snap Circuits Classic, Elenco Electronics. Downloaded from https://www.elenco.com/product/snap-circuits-300-experiments/ on Dec. 5, 2019.

\* cited by examiner

EMG DEVICE

BACKGROUND

This application relates to electromyography (EMG), and more particularly to an apparatus and method for obtaining and processing EMO signals from action potential voltages.

Electromyography (EMG) refers to evaluating electrical activity produced by skeletal muscles of subjects, such as humans and animals. In particular, EMG measures action potential voltages that neurologically activate muscles. The action potential voltages can be measured from surface electrodes, or intramuscular electrodes that are inserted into a subject's muscle. EMG can be used for therapeutic uses, such as for physical therapy or rehabilitation. EMO has also been used for entertainment, for controlling a video game or other electronic device, for example.

SUMMARY

An electromyography (EMG) device according to an aspect of the present disclosure includes a main circuit board having opposing first and second faces. A plurality of first connectors of a first type are provided on the first face, and a plurality of input contacts are provided on the second face. An EMG circuit is provided on the main circuit board. The EMG circuit is configured to utilize the input contacts as inputs to obtain an EMG input signal, and process the EMG input signal to provide an EMG output signal that is based on, but different from, the EMG input signal. For each of the input contacts, there is no conductive path directly between the input contact and any of the first connectors.

In a further embodiment of any of the foregoing embodiments, the input contacts are second connectors of a second type that is different from the first type.

In a further embodiment of any of the foregoing embodiments, the main circuit board includes a plurality of corners areas, and at least one of the first connectors and second connectors are disposed in respective ones of the corner areas.

In a further embodiment of any of the foregoing embodiments, at least one of the first connectors and second connectors are at least partially disposed in a respective opening in its respective corner area.

In a further embodiment of any of the foregoing embodiments, the first type of connectors are non-snap connectors.

In a further embodiment of any of the foregoing embodiments, the first connectors and second connectors are snap connectors.

In a further embodiment of any of the foregoing embodiments, the first and second connectors are arranged in pairs, with each pair sharing a respective central longitudinal axis, and each first connector is one of a snap stud and a snap socket, and each second connector is the other of a snap stud and a snap socket.

In a further embodiment of any of the foregoing embodiments, for each of the pairs, the first connector and second connector are connected to different nodes of the EMG circuit.

In a further embodiment of any of the foregoing embodiments, a sibling board is provided that has a plurality of connectors configured to engage the first or second connectors of the main circuit board for mounting the sibling board to the main circuit board in a mounted configuration. The main circuit board and sibling board face each other and are substantially parallel to each other in the mounted configuration.

In a further embodiment of any of the foregoing embodiments, the sibling board is a sibling circuit board and the connectors of the sibling circuit board are snap connectors. A first engagement between one of the sibling circuit board snap connectors and one of the first and second connectors shares a ground signal between the sibling circuit board and main circuit board. A second engagement between one of the sibling circuit board snap connectors and another of the first and second connectors shares a power supply voltage between the sibling circuit board and main circuit board. A third engagement between one of the sibling circuit board snap connectors and another of the first and second connectors provides the EMG output signal from the main circuit board to the sibling circuit board.

In a further embodiment of any of the foregoing embodiments, a profile and area of the sibling board is approximately the same as that of the main circuit board.

In a further embodiment of any of the foregoing embodiments, a profile and area of the sibling board differs from that of the main circuit board.

In a further embodiment of any of the foregoing embodiments, the sibling board is a protective board that does not include circuit components, and the protective board has notched edges that provide access to pin receptacles disposed along an edge of the main circuit board in the mounted configuration.

In a further embodiment of any of the foregoing embodiments, the sibling board is a sibling circuit board, and the main circuit board includes a pin receptacle that is disposed along an edge of the main circuit board and is separate from the plurality of first and second connectors. The sibling circuit board includes a pin that is received into the pin receptacle in the mounted configuration and provides for transfer of a signal between the main circuit board and sibling circuit board, the pin extending substantially parallel to the central longitudinal axes and being separate from the plurality of snap connectors of the sibling circuit board.

In a further embodiment of any of the foregoing embodiments, the signal that is transferred between the main circuit board and sibling circuit board via the pin and pin receptacle is the EMG output signal.

In a further embodiment of any of the foregoing embodiments, the EMG circuit is configured to provide a plurality of different EMG output signals that are each based on the EMG input signal.

In a further embodiment of any of the foregoing embodiments, the plurality of different EMG output signals include a first EMG output signal that is a filtered version of the EMG input signal and includes a voltage offset, a second EMG output signal that corresponds to the first EMG output signal after rectification and centering about a non-zero voltage and removal of the voltage offset, and a third EMG output signal that is an envelope signal and corresponds to an envelope of the second EMG output signal.

In a further embodiment of any of the foregoing embodiments, the EMG circuit includes a difference circuit that has an operational amplifier configured to utilize two of the first connectors to obtain respective action potential voltages, and create the EMG input signal based on a difference between the two action potential voltages. The creation of the EMG input signal introduces a voltage offset, which is not already present in the action potential voltages, that centers the plurality of EMG output signals about a non-zero voltage.

In a further embodiment of any of the foregoing embodiments, the EMG circuit includes a bandpass filter configured to receive the EMG input signal from the difference circuit and provide a filtered EMG signal as an output that excludes at least one of frequencies in the EMG input signal above a predefined upper threshold and frequencies in the EMG input signal below a predefined lower threshold.

In a further embodiment of any of the foregoing embodiments, the EMG circuit includes a rectification circuit configured to rectify the EMG input signal about the non-zero voltage to create a rectified EMG signal, and an offset removal circuit configured to receive the rectified EMG signal and provide an adjusted EMG signal in which the voltage offset is removed.

In a further embodiment of any of the foregoing embodiments, the EMG circuit includes an output circuit connected to the offset removal circuit and configured to produce the EMG output signal as an EMG envelope signal that is based on the adjusted EMG signal.

An EMG device according to an aspect of the present disclosure includes a difference circuit including an operational amplifier coupled to two action potential voltages and configured to create an EMG signal based on a difference between the two action potential voltages. The creation of the EMG signal introduces a voltage offset, not already present in the action potential voltages, that centers the EMG signal about a non-zero voltage. A bandpass filter is configured to receive the EMG signal from the difference circuit and provide a filtered EMG signal that excludes frequencies in the EMG signal that are above a predefined upper threshold and below a predefined lower threshold. A rectification circuit is configured to rectify the filtered EMG signal to create a rectified EMG signal that is centered about the non-zero voltage. An offset removal circuit is configured to receive the rectified EMG signal and provide an adjusted EMG signal in which the voltage offset is removed. An output circuit is connected to the offset removal circuit and is configured to produce an EMG envelope signal based on the adjusted EMG signal.

In a further embodiment of any of the foregoing embodiments, the EMG circuit is provided on a circuit board and includes a plurality of pairs of snap members, each pair including a snap stud and snap socket that share a respective central longitudinal axis, the snap stud extending outwards from a first face of the circuit board and the snap socket comprising a blind hole that opens to a second face of the circuit board that is opposite the first face. The EMG circuit is configured to obtain the action potential voltages through the snap sockets, and for each of the pairs, the snap stud is spaced apart from the snap socket and there is no conductive path directly between the snap stud and snap socket.

A method of obtaining EMG signals according to an aspect of the present disclosure includes receiving input voltages from a plurality of first snap connectors of a first type on a first face of a main circuit board, each first snap connector being part of a respective pair of snap members that also includes a second snap connector of a second type on a second face of the main circuit board that is opposite the first face. For each pair, the first snap connector is spaced apart from the second snap connector and there is no conductive path directly between the first and second snap connectors, and each pair shares a respective central longitudinal axis. The method includes stacking a sibling circuit board onto the main circuit board. The stacking includes engaging the first snap connectors of the main circuit board with corresponding snap connectors of the sibling circuit board. An EMG circuit on the main circuit board is utilized to obtain an EMG output signal that is based on the input voltages, and a signal from the EMG circuit on the main circuit board is provided to the sibling circuit board through one of first snap connectors of the main circuit board which engages one of the snap connectors of the sibling circuit board.

In a further embodiment of any of the foregoing embodiments, the method includes receiving a pin that extends from the sibling circuit board substantially parallel to the central longitudinal axes into a pin receptacle of the main circuit board that is disposed along an edge of the main circuit board and is separate from the first and second snap connectors of the main circuit board. A signal is transferred between the EMG circuit and the sibling circuit board through the pin and pin receptacle.

The embodiments, examples, and alternatives of described in the claims and in the following description and drawings, including any of their various aspects or respective individual features, may be taken independently or in any combination. Features described in connection with one embodiment are applicable to all embodiments, unless such features are incompatible.

DETAILED DESCRIPTION

Figure 1:
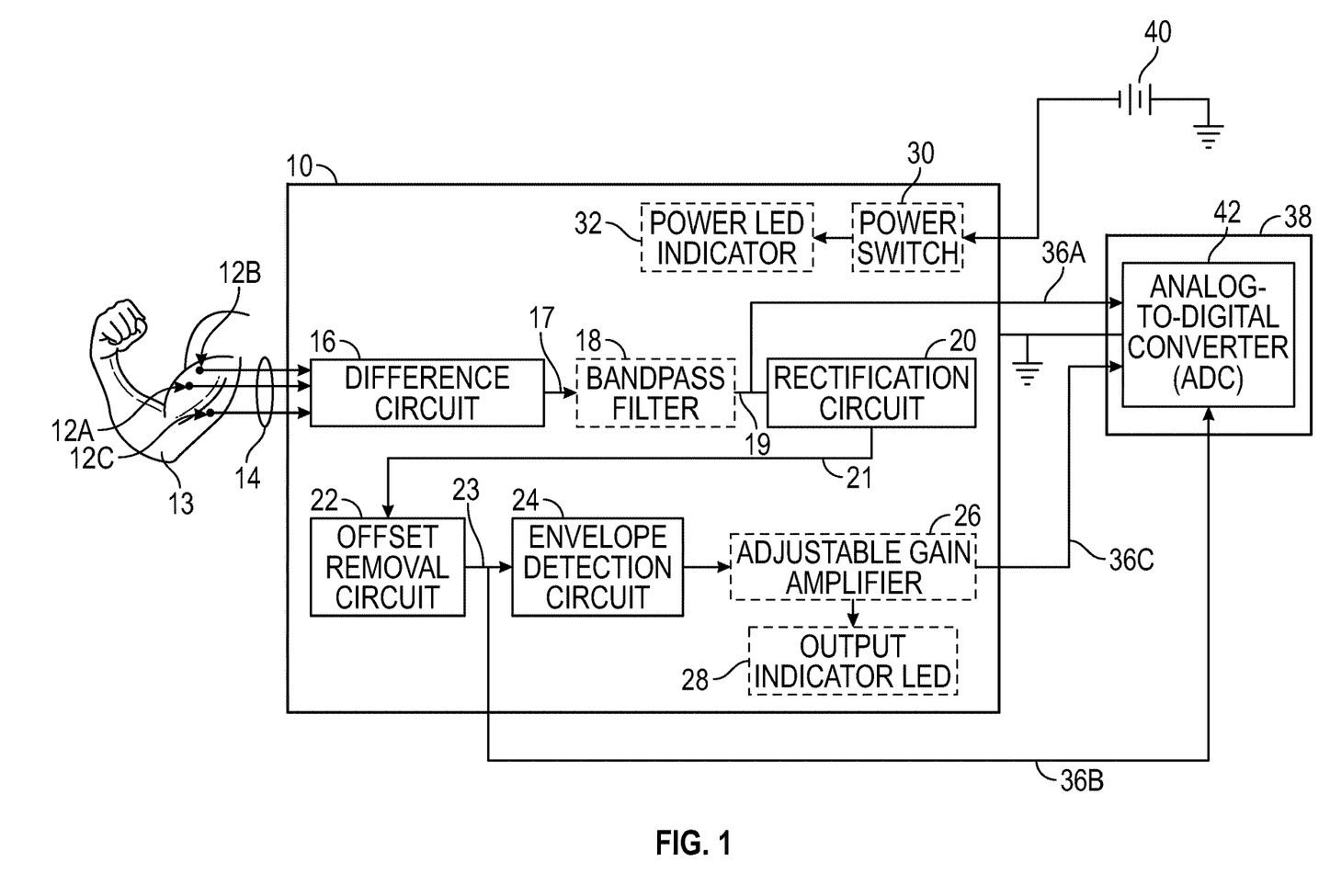
FIG. 1 schematically illustrates an example EMG circuit.

FIG. 1 schematically illustrates an example EMG circuit 10 that is electrically connected to electrodes 12A-C secured to a human subject 13. The electrodes 12A-C provide action potential voltages 14 to the EMG circuit 10. The electrodes 12A-C may be standard stick-on electrodes which a user sticks onto their skin or electrodes embedded into wearable fabric, for example.

A difference circuit 16 is configured to create an EMG input signal 17 based on a difference between two of the action potential voltages 14. The action potential voltages 14 include a voltage offset (e.g., a DC offset) prior to the creation of the EMG input signal 17 by the difference circuit 16. This will be called an "inherent voltage offset" herein because it may be inherent to the action potential voltages 14, and is not introduced by the EMG circuit 10.

In creating the EMG input signal 17, the difference circuit introduces an additional voltage offset, not already present in the action potential voltages (i.e., different from the inherent voltage offset), that centers the EMG input signal 17 about a non-zero voltage. This additional voltage offset will be called an "introduced voltage offset" herein because it is intentionally introduced by the EMG circuit 10. In one or more embodiments, the non-zero voltage about which the EMG signal is centered is $V_s/2$, where Vs is a voltage of power supply 40 of the EMG circuit 10. In some such embodiments, $V_s/2$ may serve as a virtual ground.

A bandpass filter 18 is connected to the difference circuit 16. The bandpass filter 18 is configured to filter out frequencies in the EMG input signal 17 that are above a predefined upper threshold and that are below a predefined lower threshold, where the upper threshold is greater than the lower threshold. The bandpass filter 18 is also configured to remove the inherent voltage offset. The bandpass filter 18 provides a filtered EMG signal 19 (or "raw EMG signal") that is passed to a rectification circuit 20 and that is provided as a first EMG output signal 36A. The removal of the inherent voltage offset can provide a centering of the EMG signal 119 about its reference voltage (e.g., $V_s/2$), which may otherwise be absent if the inherent voltage offset was not removed.

The rectification circuit 20 is configured to rectify the filtered EMG signal 19 about the non-zero voltage to create a rectified EMG signal 21.

An offset removal circuit 22 is configured to remove the introduced voltage offset from the rectified EMG signal 21 to create an adjusted EMG signal 23 that is provided as a second EMG output signal 36B.

An envelope detection circuit 24 is configured to receive the adjusted EMG signal 23 to produce a third EMG output signal 36C that corresponds to an envelope of the adjusted EMG signal 23.

Each of the output signals 36A-C is based on the EMG input signal 17. The output signals 36A-C can be provided to a client device 38, for example. A number of client devices 38 could be used, such as computers, tablets, smartphones, development boards (e.g., ARDUINO, RASPBERRY PI, etc.), microcontrollers, etc. Optionally, an analog-to-digital converter (ADC) 42 may be used on the client device 38 to create a digital signal for digital processing circuitry.

Optionally, an adjustable gain amplifier 26 may be included, which is configured to adjust a gain of the EMG output signal 36C. An output light-emitting diode (LED) indicator 28 may also be included, which is configured such that the EMG output signal 36 passes through the LED 28, and a luminance of the LED 28 varies based on an amplitude of the EMG output signal 36. Thus, the LED 28 may serve as a muscle activity indicator that increases in brightness as the human subject 13 flexes their muscles with a greater intensity.

A power supply 40 (e.g., a battery or some other energy storage device, such as a large capacitor) provides a supply voltage Vs that powers the EMG circuit 10. The power supply 40 could be a standalone power supply (e.g., an AC adapter), could be part of the client device 38, or could be part of a sibling circuit board, for example. A power switch 30 may be connected between the power supply 40 and the EMG circuit 10, to control whether the EMG circuit 10 is in an ON state or an OFF state. A power indicator LED 32 may be connected to the power switch to indicate whether the EMG circuit 10 is in the ON or OFF state. Components 26, 28, 30, and 32 are optional components, and may be omitted from the EMG circuit 10 in some embodiments.

By using the EMG circuit 10, a user is able to take advantage of an entire analog input range of a microcontroller or ADC 42 used by client device 38. By centering the EMG signal about a non-zero voltage (e.g., $V_s/2$), the entire EMG signal can be placed into a positive voltage plane before rectification, which can avoid loss of a "negative" portion of the waveform during rectification. Then, with subsequent removal of the introduced voltage offset, the adjusted EMG signal 23 may be provided to have a 0 volts reference voltage, so that the entire resolution of an ADC 42 can be utilized. Otherwise, a portion of the voltage range of the ADC will be squandered. Assume, for example, that an ADC has a 10-bit resolution (1024 voltage levels=$2^{10}$). If the introduced voltage offset was not removed, that voltage range may be substantially reduced, reducing the resolution to a 9-bit resolution (512 voltage levels=$2^9$), because the entire EMG signal range would be from $V_s/2$-$V_s$ instead of 0-Vs. The size of the portion of the voltage range that would be squandered depends on what non-zero voltage is used by the difference circuit 16. For example, if the difference circuit 16 centers about $V_s/2$, half of the voltage range would be squandered.

In one or more embodiments, the difference circuit 16 is an instrumentation amplifier, the offset removal circuit 22 is a difference amplifier, the envelope detector circuit 24 is an integration amplifier, and the rectification circuit 20 is either a full wave or a half wave rectification circuit.

Figure 2:
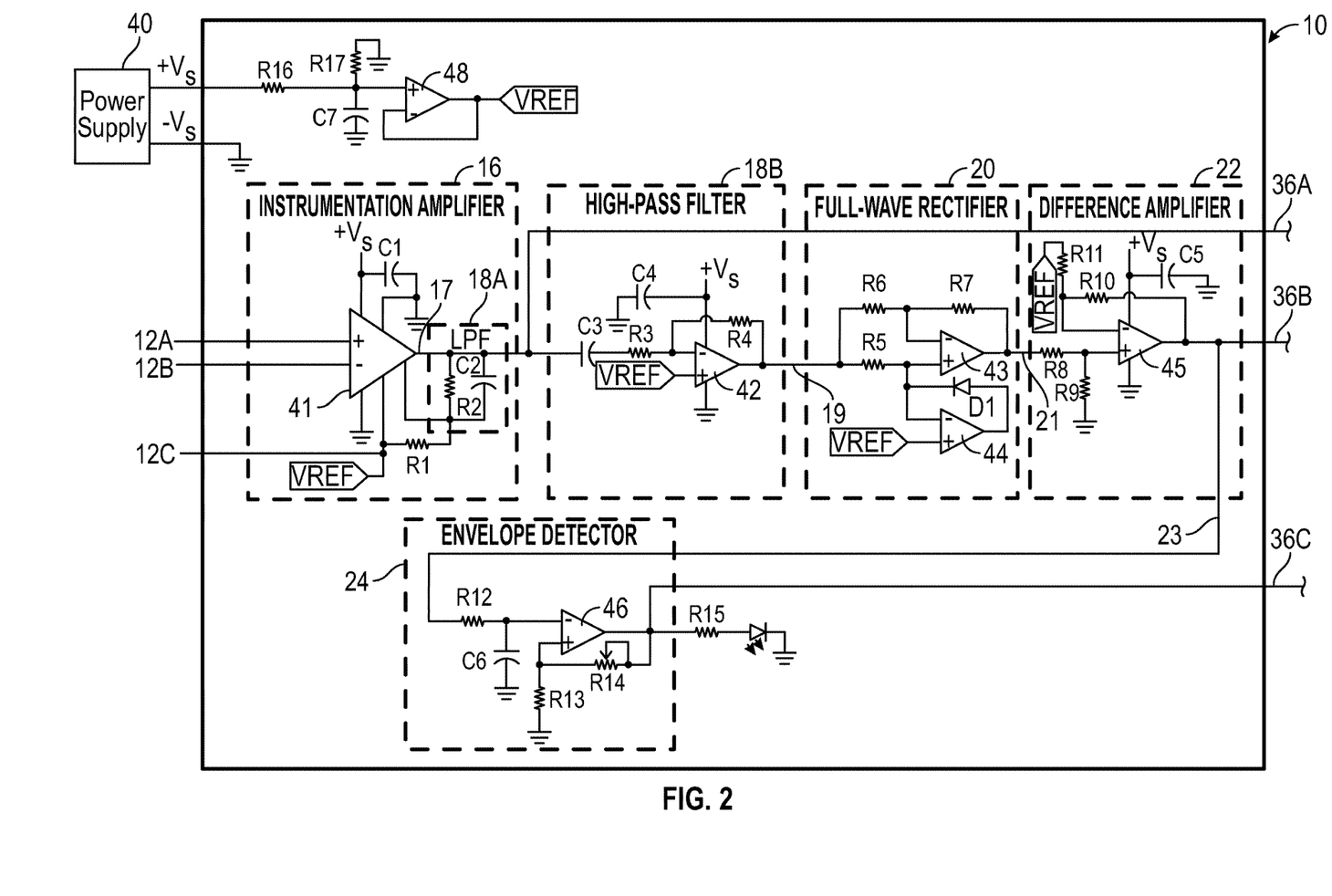
FIG. 2 illustrates an example embodiment of the EMG circuit of FIG. 1.

FIG. 2 illustrates an example embodiment of the EMG circuit of FIG. 1. In the example of FIG. 2, the difference circuit 16 is an instrumentation amplifier that creates an EMG input signal 17 based on a difference between two action potential voltages of electrodes 12A and 12B respectively. Electrode 12C provides a reference voltage of a subject to which the electrode 12C is attached. This could be used, for example, to determine a ground signal of the subject to which electrode C is attached.

The instrumentation amplifier includes operational amplifier (op-amp) 41, resistors R1 and R2, and capacitors C1 and C2. Resistor R2 and capacitor C2 also form part of a low pass filter 18A, which together with the high-pass filter 18B form the bandpass filter 18.

The high-pass filter 18B includes op-amp 42, resistors R3 and R4, and capacitors C3 and C4.

In the example of FIG. 2, the rectification circuit 20 is a full-wave rectifier that takes the portion of the EMG signal that dips below the non-zero voltage about which the EMG signal is centered (e.g., Vs/2) and inverts that portion. The full-wave rectifier includes op-amps 43 and 44, resistors R5, R6, and R7, and diode D1.

In the example of FIG. 2, the offset removal circuit 22 which removes the introduced voltage offset is a difference amplifier that includes resistors R8, R9, R10, and R11, capacitor C5, and op-amp 45.

In the example of FIG. 2, the envelope detection circuit 24 is a low-pass filter connected to a non-inverting amplifier that includes resistors R12 and R13, capacitor C6, and op-amp 46. The non-inverting amplifier may also act as an adjustable gain amplifier by including potentiometer R14.

Output indicator LED 28 is connected to the EMG envelope signal 36C via resistor R15.

Power supply 40 has a positive terminal that provides a voltage Vs and also has a negative terminal. Resistors R16 and R17 act as a voltage divider to lower the voltage Vs to Vs/2. Capacitor C7 and resistor R16 act as a low-pass filter to remove AC voltage signals from Vs. Op-amp 48 acts as a buffer amplifier to prevent impedance loading and interference. An output of op-amp 48, which may be Vs/2, is connected to a voltage potential of a subject from which the first and second action potential voltages originate (via electrode 12C) to form a reference voltage $V_{REF}$. This may be used to effectively synchronize the subject's body electrical potential to the electrical potential of the EMG circuit 10. A negative terminal of the power supply 40 provides a ground connection for the EMG circuit 10.

Figure 3A:
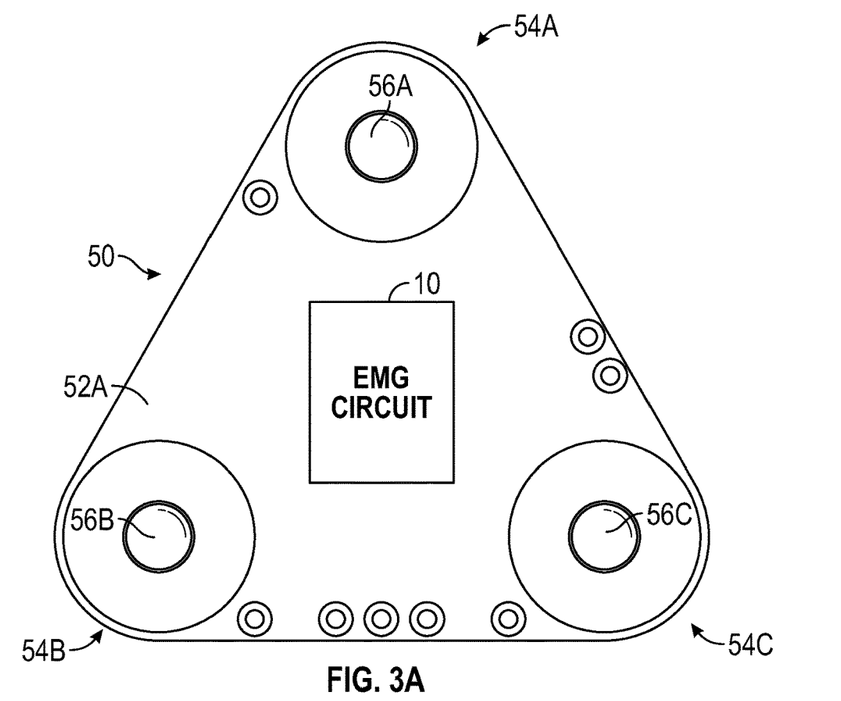
FIG. 3A illustrates a first face of an example circuit board that includes at least a portion of the EMG circuit of FIG. 1.
Figure 3B:
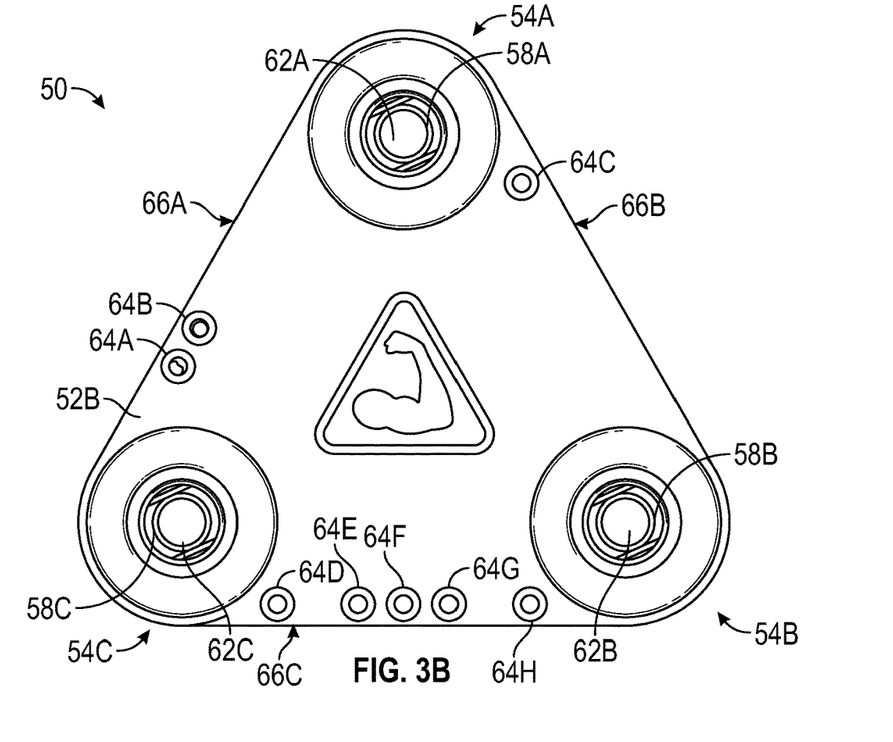
FIG. 3B illustrates a second face of the circuit board of FIG. 3 that is opposite the first face.
Figure 3C:
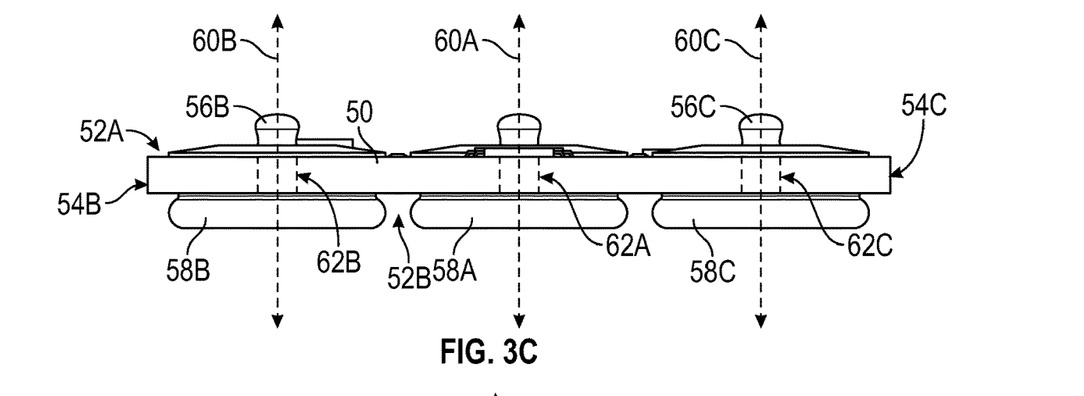
FIG. 3C illustrates a side view of the example circuit board of FIG. 3A.

FIG. 3A illustrates a first face 52A of an example circuit board 50 on which some or all of the EMG circuit 10 may be disposed. FIG. 3B illustrate a second face 52B of the circuit board 50 that is opposite the first face 52A. FIG. 3C illustrates a side view of the circuit board 50.

The circuit board 50 is depicted in FIGS. 3A-C as being a triangle with sides of approximately equal length. However, it is understood that this is only an example and that other shapes could be used, such as shapes having other quantities of corners. Also, although the faces 52A-B of the circuit board 50 are depicted in FIGS. 3A-C as being are planar faces, it is understood that the faces 52A-B could be nonplanar if desired.

Referring to FIGS. 3A-C, the circuit board 50 includes a plurality of pairs of snap members, with each pair including a first snap connector stud 56 and a second snap connector 58. In the example of FIGS. 3A-C, the first snap connectors 56A-C are snap studs, and the second snap connectors 58A-C are snap sockets. However, it is understand that other arrangements could be used (e.g., all snap studs, all snap connectors, a mixture of snap studs and snap connectors on each face 52A-B, snap sockets for snap connectors 56A-C and snap studs for snap connectors 58A-C, etc.).

In the example of FIGS. 3A-C, each pair shares a respective central longitudinal axis 60. Thus, the pair of snap stud 56A and snap socket 58A share central longitudinal axis 60A, the pair of snap stud 56B and snap socket 58B share central longitudinal axis 60B, and the pair of snap stud 56C and snap socket 58C share central longitudinal axis 60C. The central longitudinal axes 60A-C are substantially parallel to each other. The circuit board 50 includes three corner areas 54A-C, each one of the pairs is disposed in a respective one of the corner areas 54A-C.

The circuit board 50 includes a plurality of openings 62A-C, and each snap socket 58B is at least partially disposed in a respective one of the openings 62A-C. The snap studs 56 extend outwards from the first face 52A, and the snap sockets 58 each include a blind hole 61 that opens to the second face 52B.

The snap sockets 58 are configured to receive the electrodes 12A-C of FIG. 1. In one example, one of the snap sockets 58 connects electrode 12A to the EMG circuit 10, another of the snap sockets 58 connects electrode 12B to the EMG circuit 10, and another of the snap sockets 58 connects electrode 12C to the EMG circuit. The EMG circuit 10 is configured to use the snap sockets 58 as inputs to obtain the EMG input signal 17, and as discussed above, is further configured to provide at least one EMG output signal 36 that is based on, but different from, the EMG input signal 17.

For each of the pairs of snap members, the snap stud 56 is spaced apart from the snap socket 58, and there is no conductive path directly between the snap stud 56 and snap socket 58. Instead, the snap stud 56 and snap socket 58 of each pair are connected to different nodes of the EMG circuit 10. In the same or another example, one of the snap studs 56 connects to a ground node of the EMG circuit 10, another of the snap studs 56 connects to a +Vs node of the EMG circuit 10, and another of the snap studs 56 connects to a node of the EMG output 36C. The snap studs 56 can be used to attach a sibling board to the circuit board 50 (e.g., a sibling circuit board or sibling protective board that omits circuit components).

In one embodiment, EMG circuit 10 is sized for wearing on the subject's body. In one such example, the first snap connectors 56 are approximately 0.5-2 inches apart from each other. In a further embodiment, the first snap connectors 56 are 0.75-1.25" apart from each other. In such examples, the second snap connectors 58 could be the same distance apart from each other. These relatively small distances between the pairs make the circuit board 50 suitable for wearing on a limb (e.g., an arm) of the human subject 13.

Figure 4A:
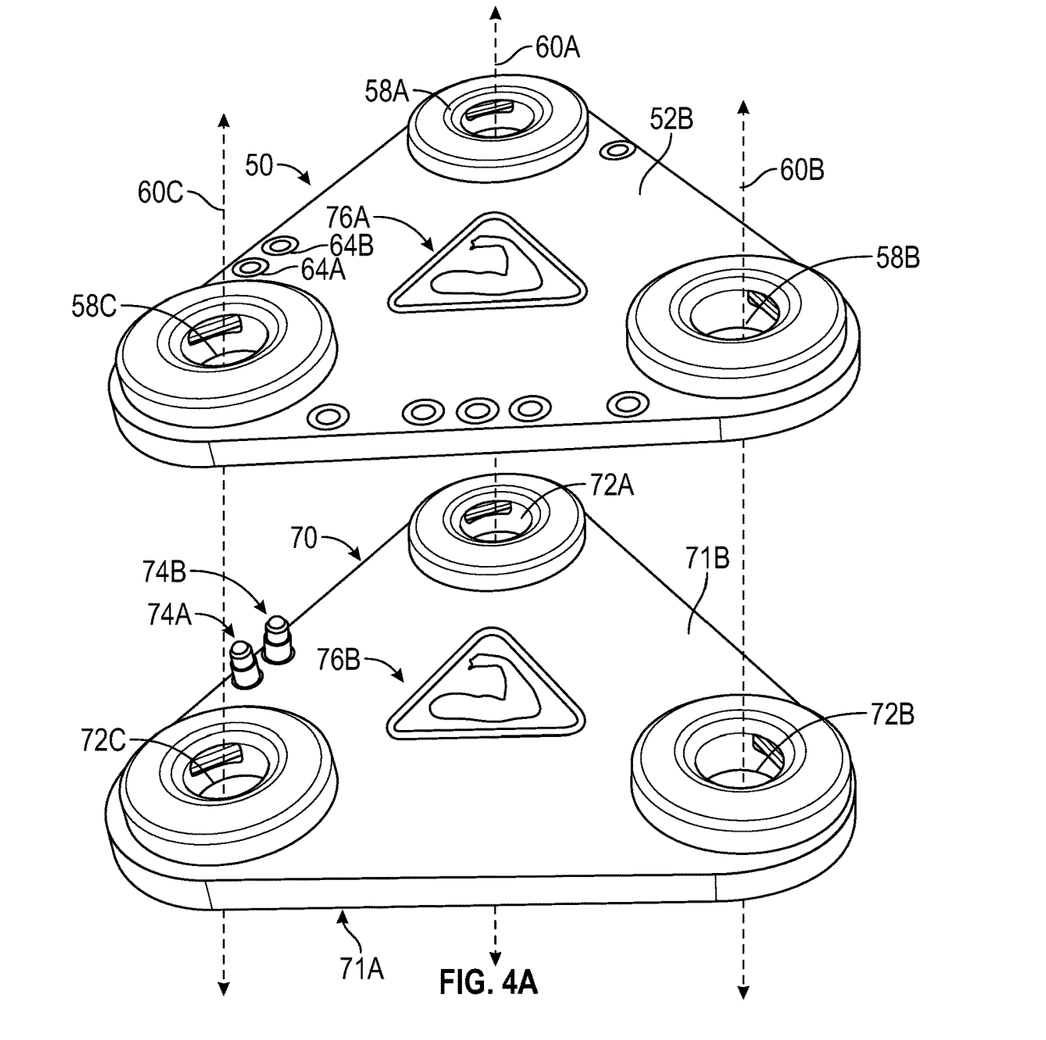
FIG. 4A illustrates a perspective of the circuit board of FIG. 3A and a sibling circuit board that can mount to the circuit board.
Figure 4B:
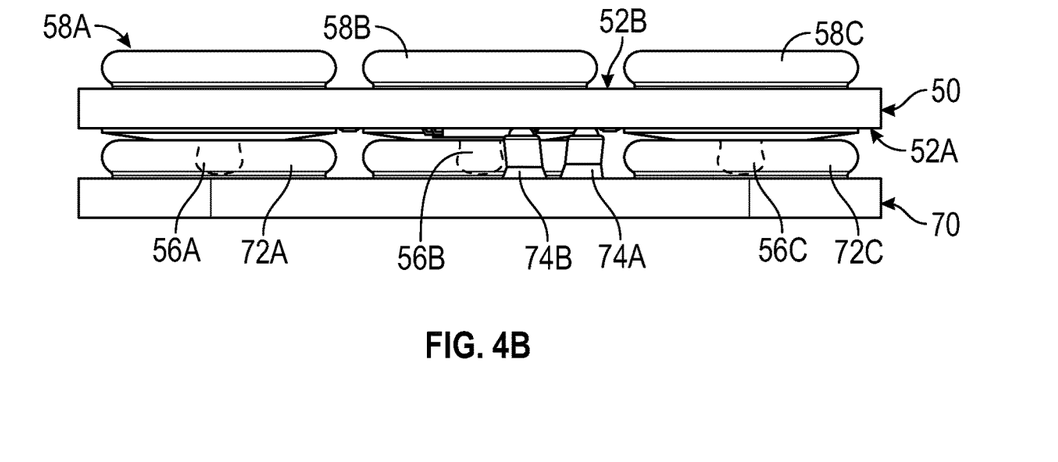
FIG. 4B illustrates a side view of the sibling circuit board of FIG. 4A mounted to the circuit board of FIG. 3A.

FIG. 4A is a perspective of the circuit board 50 and sibling circuit board 70 prior to mounting, and FIG. 4B is a side view of the circuit board 50 and sibling circuit board 70 in a mounted configuration.

Referring now to FIGS. 4A-B, the sibling circuit board 70 includes opposing first and second faces 71A-B. Like the circuit board 50, the sibling circuit board 70 also includes a plurality of snap sockets 72A-C. In the mounted configuration of FIG. 4B, each snap stud 56A-C of the circuit board 50 is received into a respective one of the snap sockets 72A-C, and a central longitudinal axis of each snap socket 72 is coaxial with the central longitudinal axis 60 of its associated snap stud 56.

Prior to being mounted, the circuit board 50 and sibling circuit board 70 can be vertically aligned as shown in FIG. 4A.

In the mounted configuration, the circuit board 50 and sibling circuit board 70 are arranged a stacked configuration such that the circuit boards 50, 70 are substantially parallel, face each other, are spaced apart from each other, and are electrically connected through at least one of the snap studs 56 and snap sockets 72. The sibling board 70 can be dismounted from the circuit board 50 by separating the snap studs 56 of the circuit board 50 from the snap sockets 72 of the sibling circuit board 70.

The sibling circuit board 70 may be used to piggyback on the functionality of the circuit board 50 and/or to augment the functionality of the circuit board 50 in a modular fashion. The sibling circuit board 70 could be used to provide a power supply, to provide wireless capabilities, to connect one or more electrodes to the circuit board 50 (e.g., if a human subject 13 did not want to wear the circuit board 50), and/or to provide an electronic display, for example.

In the example of FIGS. 4A-B, a profile and area of the circuit board 50 is approximately the same as that of the sibling circuit board 70. Of course, it is understood that this is a non-limiting example, and that other arrangements could be provided in which a profile and/or area of the circuit board 50 different from that of the sibling circuit board 70.

Referring again to FIG. 3B, the circuit board 50 includes a plurality of pin receptacles 64 disposed along edges 66A-C of the circuit board that are separate from the plurality of snap sockets 58A-C.

An example configuration of the pin receptacles 64 is described below. Pin receptacle 64A could provide a connection to the EMG output signal 36A. Pin receptacle 64B could provide a connection to the EMG output signal 36B. Pin receptacle 64C could provide a connection to the reference voltage "$V_{REF}$" shown in FIG. 2. Pin receptacle 64D could provide access to electrode 12A. Pin receptacle 64E could provide a connection to the supply voltage +Vs. Pin receptacle 64F could provide a connection to the ground of the EMG circuit 10. Pin receptacle 64G could provide a connection to the EMG output signal 36C. Pin receptacle 64H could provide a connection to electrode 12B. Of course, other pin configurations could be used.

Referring now to FIG. 4A, the sibling circuit board 70 includes two pins 74A-B that extend substantially parallel to the central longitudinal axes 60A-C, and are separate from the plurality of snap sockets 72A-C of the sibling circuit board 70.

The pins 74A-B are for connecting to the pin receptacles 64A-B of the circuit board 50 in the mounted configuration for transferring signals between the main circuit board 50 and sibling circuit board 70. Thus, using the example from above, pin 74A could provide access to the EMG output signal 36A to the sibling circuit board 70 by connecting to pin receptacle 64A, and pin 74B could provide access to the EMG output signal 36B to the sibling circuit board 70 by connecting to pin receptacle 64B.

Referring to FIG. 4A, the circuit board 50 and sibling circuit board 70 each include respective complementary graphical indicators 76A-B for indicating a proper orientation of the circuit boards 50, 70 before being mounted. In the example of FIG. 4A, the graphical indicators depict a flexed bicep. Of course, different graphical indicators could be used. By aligning the graphical indicators 76A-B before mounting, a user can avoid inserting the pins 74A-B into an incorrect pin receptacle 64 and can also avoid creating undesired electrical connections between the snap studs 56 and snap sockets 72.

Figure 5:
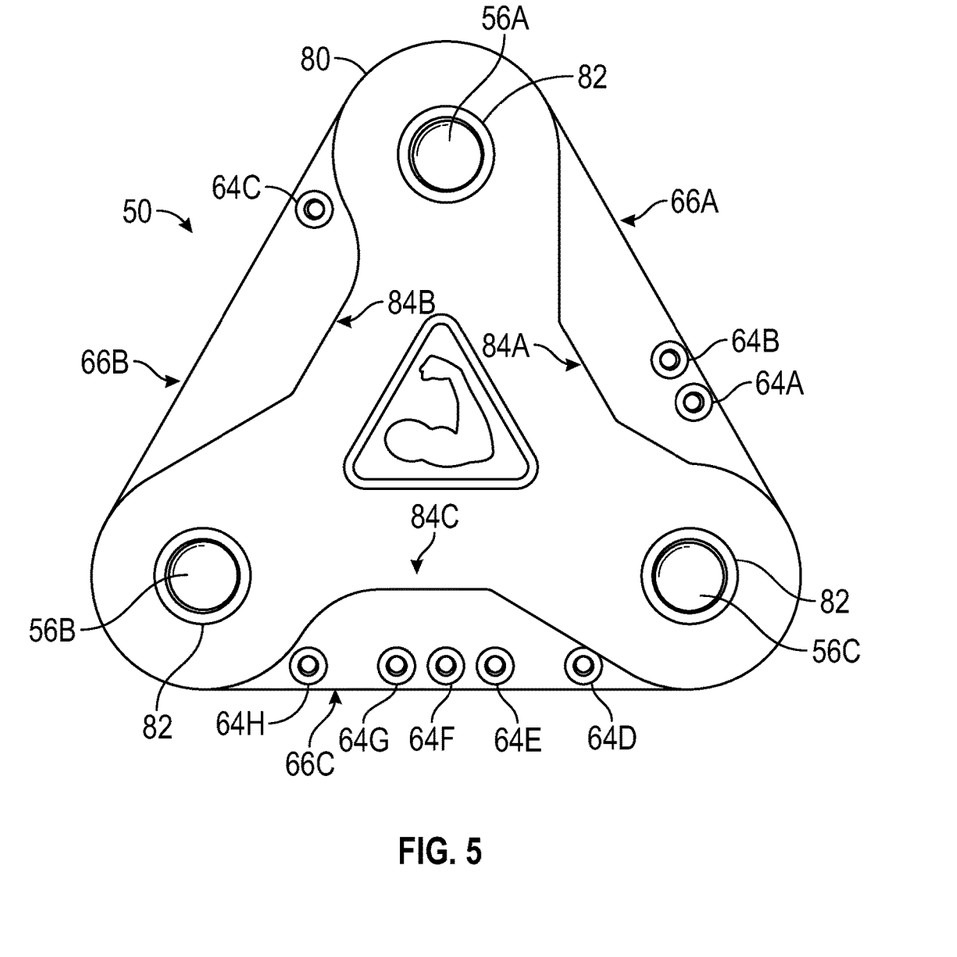
FIG. 5 illustrates a view of a protective board mounted to the circuit board of FIG. 3A.

FIG. 5 illustrates a view of a protective board 80 that is removably mounted to the circuit board 50. The protective board 80 may be a blank PCB with no circuit components on it, for example. The protective board 80 includes a plurality of socket openings 82A-C that are sized to receive and engage the snap studs 56 in the mounted configuration. In an alternative embodiment, the openings 82A-C are blind holes such that the snap studs 56 are concealed within the openings 82 and not accessible through the openings 82 in the mounted configuration. The socket openings 82A-C may non-snap sockets in some embodiments, or alternatively may be snap sockets.

The protective board 80 has notched edges 84A-C that provide access to pin receptacles 64A-H disposed along the edges 66A-C of the circuit board 50 in the mounted configuration. The protective board 80 protects the EMG circuit 10, and also provides protection against a user inadvertently touching the snap studs 56A-C and creating an inadvertent electrical connection to the associated electrical signals of the snap studs 56A-C.

Although a particular embodiment has been depicted in FIGS. 3A-C and 4A-B, it is understood that other embodiments could be implemented. For example, non-snap connectors could be used in place of the snap connectors 56 and/or 58 (e.g., a contact having a generally planar outer surface suitable for abutment against a user's body without the use of adhesive electrodes, a magnetic connector, a pin-based connector, etc).

In one example, the snap connectors 56, 58 are not arranged in pairs, but are rather offset from each other (e.g., are disposed in different corners of a six-cornered polygon circuit board). In one example, the quantity of first connectors 56 differs from the quantity of second connectors 58.

In this disclosure, like reference numerals designate like elements where appropriate and reference numerals with the addition of one-hundred or multiples thereof designate modified elements that are understood to incorporate the same features and benefits of the corresponding elements.

Figure 6:
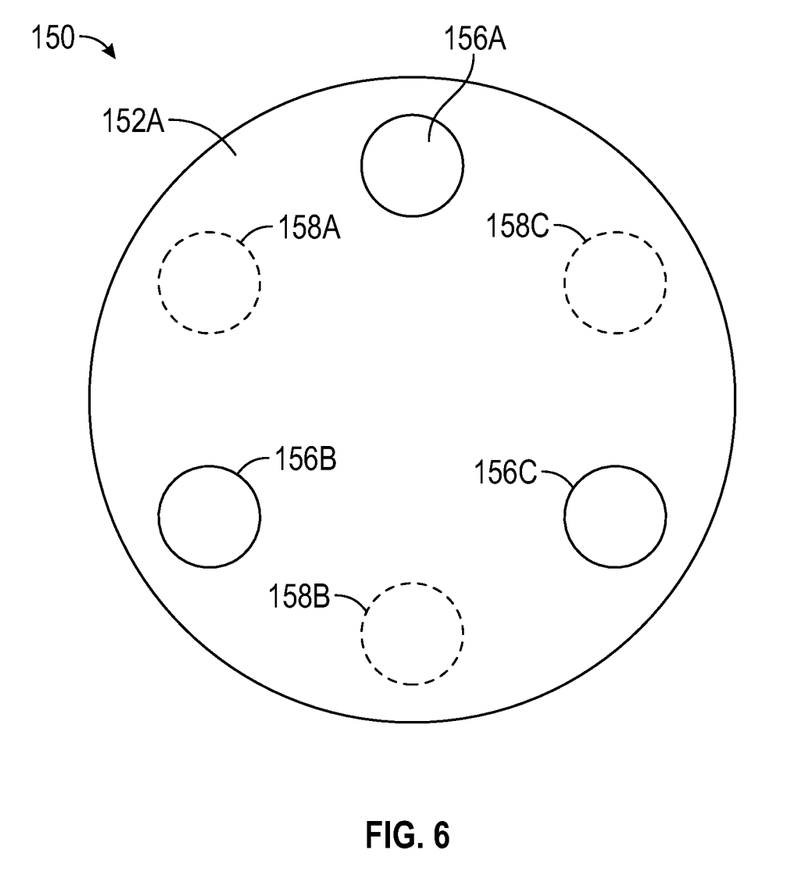
FIG. 6 illustrates a view of another example circuit board that could include at least a portion of the EMG circuit of FIG. 1.

FIG. 6 illustrates a view of another example circuit board 150 that could include at least a portion of the EMG circuit 10 of FIG. 1. In the example of FIG. 6, the circuit board 150 is circular and lacks "corner" areas. Also, in the example of FIG. 6, the connectors 156A-C on the side 152A of the circuit board 150 (e.g., snap connectors) are offset from the connectors 158A-C (e.g., snap connectors) on the opposite second side of the circuit board 150.

Although example embodiments have been disclosed, a worker of ordinary skill in this art would recognize that certain modifications would come within the scope of this disclosure. For that reason, the following claims should be studied to determine the scope and content of this disclosure.

What is claimed is:

1. An electromyography (EMG) device, comprising:
a main circuit board having opposing first and second faces;
an EMG circuit provided on the main circuit board;
a plurality of first connectors provided on the first face, wherein each first connector is configured to provide attachment to the first face;
a plurality of second connectors provided on the second face, wherein each second connector is configured to provide attachment to the second face;
wherein the EMG circuit is configured to:
utilize the second connectors as inputs to obtain an EMG input signal; and
process the EMG input signal to provide an EMG output signal that is based on, but different from, the EMG input signal;
wherein each of the first connectors and second connectors is connected to a different respective node of the EMG circuit, and there is no conductive path directly between any of the first connectors and any of the second connectors; and
wherein the first connectors and second connectors are either snap-fit connectors or magnetic connectors.

2. The EMG device of claim 1, wherein:
the main circuit board comprises at least three corner areas; and
at least one of the first connectors and second connectors are disposed in respective openings in respective ones of the at least three corner areas.

3. The EMG device of claim 1, wherein the first connectors and the second connectors are snap-fit connectors.

4. The EMG device of claim 3, wherein:
the first connectors and second connectors are arranged in pairs, with each pair sharing a respective central longitudinal axis; and
each of the plurality of first connectors is one of a snap stud and a snap socket, and each of the plurality of second connectors is the other of the snap stud and the snap socket.

5. The EMG device of claim 1, comprising:
a sibling board, which has a plurality of snap-fit connectors configured to engage the plurality of first connectors for mounting the sibling board to the main circuit board in a mounted configuration;
wherein the main circuit board and the sibling board face each other and are substantially parallel to each other in the mounted configuration.

6. The EMG device of claim 5, wherein:
the sibling board is a sibling circuit board;
a first engagement between one of the sibling circuit board snap-fit connectors and one of the first and second connectors shares a ground signal between the sibling circuit board and the main circuit board;
a second engagement between one of the sibling circuit board snap-fit connectors and another of the first and second connectors shares a power supply voltage between the sibling circuit board and the main circuit board; and
a third engagement between one of the sibling circuit board snap connectors and another of the first and second connectors provides the EMG output signal from the main circuit board to the sibling circuit board.

7. The EMG device of claim 5, wherein a profile and area of the sibling board is approximately the same as that of the main circuit board.

8. The EMG device of claim 5, wherein a profile and area of the sibling board differs from that of the main circuit board.

9. The EMG device of claim 8, wherein:
the sibling board is a protective board that does not include circuit components, the protective board having notched edges that provide access to pin receptacles disposed along an edge of the main circuit board in the mounted configuration.

10. The EMG device of claim 5, wherein:
the sibling board is a sibling circuit board;
the first connectors and second connectors are arranged in pairs, with each pair sharing a respective central longitudinal axis;
the main circuit board comprises a pin receptacle that is disposed along an edge of the main circuit board and is separate from the plurality of first and second connectors; and
the sibling circuit board comprises a pin that is received into the pin receptacle in the mounted configuration and provides for transfer of a signal between the main circuit board and the sibling circuit board, the pin extending substantially parallel to the central longitudinal axes and being separate from the plurality of snap-fit connectors of the sibling circuit board.

11. The EMG device of claim 10, wherein the signal that is transferred between the main circuit board and the sibling circuit board via the pin and the pin receptacle is the EMG output signal.

12. The EMG device of claim 1, wherein:
the EMG circuit is configured to provide a plurality of different EMG output signals that are each based on the EMG input signal; and
the plurality of different EMG output signals include:
a first EMG output signal that is a filtered version of the EMG input signal and includes a voltage offset;
a second EMG output signal that corresponds to the first EMG output signal after rectification and centering about a non-zero voltage and removal of the voltage offset; and
a third EMG output signal that is an envelope signal and corresponds to an envelope of the second EMG output signal.

13. The EMG device of claim 1, wherein the EMG circuit comprises:
a difference circuit that includes an operational amplifier configured to utilize two of the first connectors to obtain respective action potential voltages, and create the EMG input signal based on a difference between the two action potential voltages, wherein creation of the EMG input signal introduces a voltage offset, which is not already present in the action potential voltages, that centers the EMG output signal about a non-zero voltage.

14. The EMG device of claim 13, wherein the EMG circuit comprises:
a bandpass filter configured to receive the EMG input signal from the difference circuit and provide a filtered EMG signal as an output that excludes at least one of frequencies in the EMG input signal above a predefined upper threshold and frequencies in the EMG input signal below a predefined lower threshold.

15. The EMG device of claim 14, wherein the EMG circuit comprises:

a rectification circuit configured to rectify the EMG input signal about the non-zero voltage to create a rectified EMG signal; and
an offset removal circuit configured to receive the rectified EMG signal and provide an adjusted EMG signal, in which the voltage offset is removed.

16. The EMG device of claim 15, wherein the EMG circuit comprises:
an output circuit connected to the offset removal circuit and configured to produce the EMG output signal as an EMG envelope signal that is based on the adjusted EMG signal.

17. The EMG device of claim 1, wherein the plurality of first connectors are circumferentially offset from the plurality of second connectors.

18. The EMG device of claim 1, wherein each of the first connectors and second connectors has a respective central longitudinal axis, and wherein none of the central longitudinal axes are coaxial with any of the other central longitudinal axes.

19. The EMG device of claim 1, wherein the first connectors and the second connectors are both magnetic connectors.

20. An electromyography (EMG) device, comprising:
a main circuit board having opposing first and second faces;
a plurality of first snap-fit connectors provided on the first face, wherein each first snap-fit connector is configured to provide attachment to the first face;
a plurality of second snap-fit connectors, which are input connectors, provided on the second face, wherein each second snap-fit connector is configured to provide attachment to the second face; and
an EMG circuit provided on the main circuit board and configured to:
utilize the input connectors as inputs to obtain an EMG input signal; and
process the EMG input signal to provide an EMG output signal that is based on, but different from, the EMG input signal;
wherein for each of the input connectors, there is no conductive path directly between the input connector and any of the first snap-fit connectors.

21. The EMG device of claim 20, wherein each of the first snap-fit connectors and second snap-fit connectors is connected to a different respective node of the EMG circuit.

22. The EMG device of claim 20, wherein:
each of the plurality of first connectors is one of a snap stud and a snap socket, and each of the plurality of second connectors is the other of the snap stud and the snap socket.

23. An electromyography (EMG) device, comprising:
a main circuit board having opposing first and second faces;
a plurality of first connectors provided on the first face, wherein each first connector is configured to provide attachment to the first face;
a plurality of second connectors, which are input connectors, provided on the second face; and
an EMG circuit provided on the main circuit board and configured to:
utilize the input connectors as inputs to obtain an EMG input signal; and
process the EMG input signal to provide an EMG output signal that is based on, but different from, the EMG input signal;

wherein the first connectors and second connectors are arranged in pairs, with each pair sharing a respective central longitudinal axis; and wherein for each of the pairs, there is no conductive path directly between the first connector and the second connector.

\* \* \* \* \*